United States Patent [19]

Fruehwirth

[11] Patent Number: Plant 7,309

[45] Date of Patent: Aug. 28, 1990

[54] POINSETTIA PLANT '7-81'

[75] Inventor: Franz Fruehwirth, Encinitas, Calif.

[73] Assignee: Paul Ecke Ranch, Inc., Encinitas, Calif.

[21] Appl. No.: 263,495

[22] Filed: Oct. 27, 1988

[51] Int. Cl.[5] ..... A01H 5/00

[52] U.S. Cl. ..... Plt./86

[58] Field of Search ..... Plt./86

*Primary Examiner*—James R. Feyrer

*Attorney, Agent, or Firm*—Arnold, White & Durkee

[57] ABSTRACT

A new Poinsettia cultivar, named '7-81', particularly distinguished by its bicolored, pink on white bracts as described. '7-81' originated as a sport of the cultivar of U.S. Plant Pat. No. 5,497. Bract characteristics are similar to those of the cultivar of U.S. Plant Pat. No. 4,384, yet with pink color of the bracts that is softer, with a bicolor contrast less than that of the cultivars of U.S. Plant Pat. Nos. 4,810 or 3,393.

1 Drawing Sheet

BACKGROUND OF THE INVENTION

The Poinsettia of the present invention is a cultivar having the same physical traits and growth characteristics as the red bracted cultivar of the U.S. Plant Pat. No. 4,384, except that this new plant has bicolored, pink on white flower bracts.

This new Poinsettia cultivar originated as a sport of the cultivar of U.S. Plant Pat. No. 5,497 in a greenhouse in Encinitas, Calif. It was selected because of traits which distinguish it from other poinsettia cultivars and seem to make it a desirable plant for commercial greenhouse production. It has all of the desirable vigor, self-branching and large flower bract characteristics as the other color sports of the U.S. Plant Pat. No. 4,384 cultivar. The pink color in the bracts is softer and the bicolor contrast is less than in the cultivar of U.S. Plant Pat. No. 4,810 or U.S. Plant Pat. No. 3,393. After selection, vegetatively reproduction of this plant by stem cuttings for test purposes in Encinitas, Calif., and clones of the plant were subjected to successive generations of vegetative propagation. The physical traits and growth characteristics remain stable from generation to generation.

DESCRIPTION OF THE PHOTOGRAPHS

'7-81' is illustrated in the accompanying color photographs. The upper photo is a side view of a typical unpinched plants in full flower. The lower photo is a top view of a plant showing flower and bract formation.

DESCRIPTION OF THE PLANT

The following is a detailed description of this new Poinsettia as observed in a greenhouse in Encinitas, Calif., during December, 1987. Recorded observations from flowering plants, grown as 3 unpinched plants per pot were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of the cultivar of U.S. Plant Pat. No. 5,497.

Classification:

*Botanic.*—*Euphorbia pulcherrima* Willd.

*Common name.*—Poinsettia.

*Cultivar name.*—'7-81'.

Form: Shrub.

Height: Medium.

Growth habit: As a single stemmed plant, upright and vigorous. In full flower, the stem is terminated by a large inflorescence, with several smaller flowering side shoots lower on the stem. Observation of 3 plants in a pot with an overall height of 38 cm. and an overall width of 48 cm. were made. The bract diameter of individual flowers was 32 cm.

Branching: Branching can be enhanced by removal of the stem tip. Then, several flowering branches with equal vigor may develop on a single plant.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 14–16 cm. long and about 10–11 cm. wide with leaf petioles about 5–6 cm. long.

Leaf shape: Typical leaves are ovate with obtuse bases and acuminate tips. Leaf margins are mostly lobed, with 1–2 lobes and numerous small marginal minor indentations on each side of the leaf blade.

Color:

*Upper side.*—Darker than RHS 137A.

*Under side.*—Near RHS 137C.

Retention: The foliage retention is good even under low light intensities in the consumer's home.

Bracts: Generally there are 24–27 bicolored pink on white bracts of various sizes subtending the cyathia. The primary bracts have blades typically 15–17 cm. long and 10 cm. wide with petioles about 2–3 cm. long.

Shape: Bracts are mostly ovate with acute bases and acuminate tips. Primary bracts are mostly entire with some slight lobing.

Color:

*Upper side.*—Bicolored: Pink on white bracts. White background near RHS 155A. Pink marbling near RHS 51D.

*Under side.*—Bicolored: White near RHS 155A. Pink near RHS 51D.

Cyathia: Generally, 12–15 cyathia (flowers) are present when the plant is in "full bloom". Each cyathium is about 7–8 mm long and about 5 mm wide, light green in color, but fading to a yellowish fringe at the distal end. Usually, one bright yellow nectar cup protrudes from the side of the cyathium. The flower pedicel is also light green and about 3–4 mm long. The anthers protruding from the cyathia are white.

What is claimed:

1. A new and distinct Poinsettia cultivar, substantially as herein shown and described, distinguished by its bicolored, pink on white bracts.

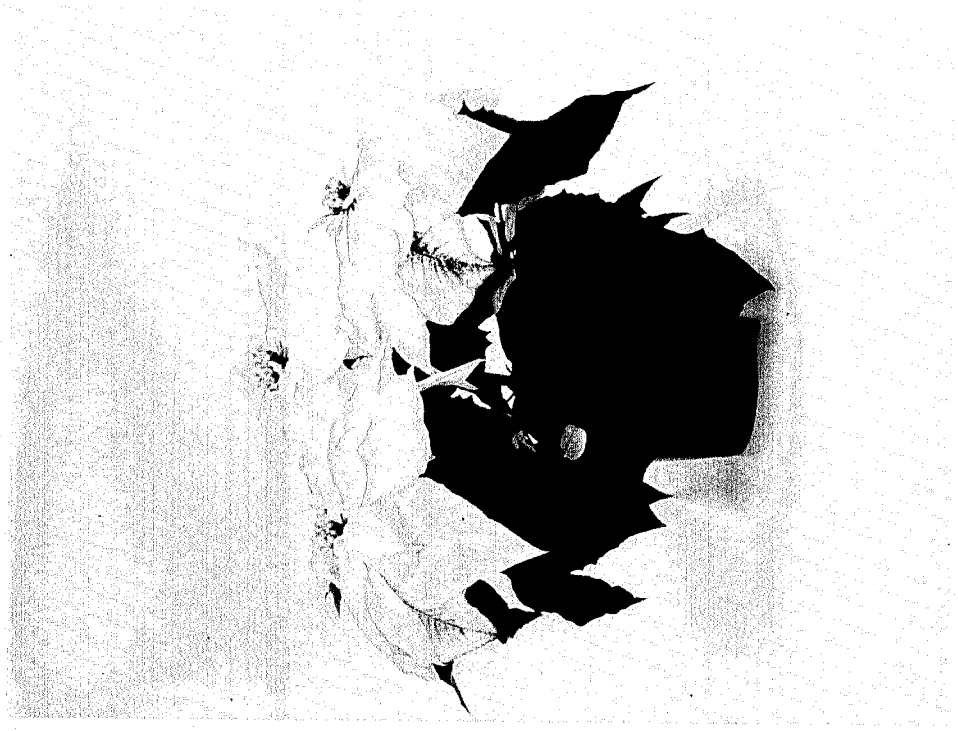
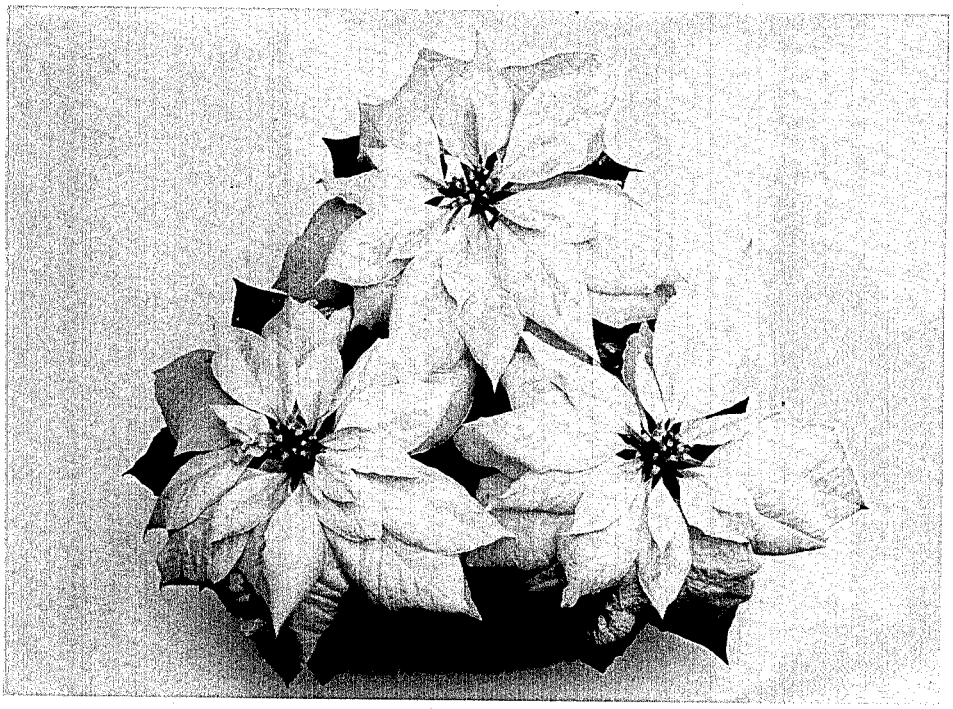

* * * * *